(12) United States Patent
Garberoglio

(10) Patent No.: US 6,290,719 B1
(45) Date of Patent: *Sep. 18, 2001

(54) ELEMENT FOR ANCHORING AN IMPLANT DEVICE IN PLACE

(75) Inventor: Bruno Garberoglio, Turin (IT)

(73) Assignee: Sorin Biomedica Cardio S.p.A. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/115,404

(22) Filed: Jul. 14, 1998

(30) Foreign Application Priority Data

Aug. 13, 1997 (IT) .............................. TO97A0743

(51) Int. Cl.⁷ ...................................... A61F 2/06
(52) U.S. Cl. ................................. 623/1; 623/12
(58) Field of Search .................. 623/1, 11, 12; 606/195

(56) References Cited

U.S. PATENT DOCUMENTS

| | | |
|---|---|---|
| 4,913,147 | 4/1990 | Fahlstrom et al. . |
| 5,037,427 * | 8/1991 | Harada .................................. 606/108 |
| 5,523,092 | 6/1996 | Hanson et al. . |
| 5,662,675 * | 9/1997 | Polanskyj-Stockert ............... 606/194 |
| 5,681,346 * | 10/1997 | Orth ......................................... 623/1 |

FOREIGN PATENT DOCUMENTS

| | | |
|---|---|---|
| 657147 * | 6/1995 | (EP) ......................................... 623/1 |
| 2 731 610 A1 | 9/1996 | (FR) . |
| 2 736 257 A1 | 1/1997 | (FR) . |

* cited by examiner

*Primary Examiner*—Michael J. Milano
(74) *Attorney, Agent, or Firm*—Popovich & Wiles, P.A.

(57) ABSTRACT

The anchorage element (3) includes a body made of shape memory material which, on reaching a transition temperature, passes from a generally retracted position with respect to the associated implant device (1) to an expanded position in which the element (3) anchors the device (1) to the implant site.

12 Claims, 1 Drawing Sheet

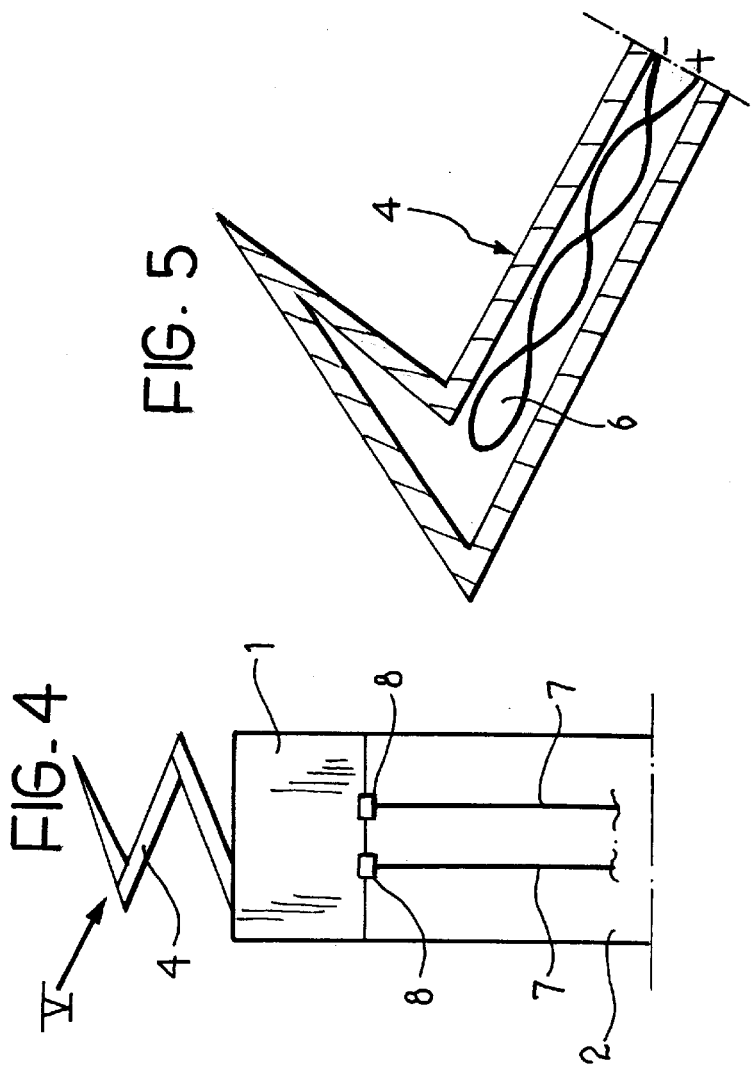
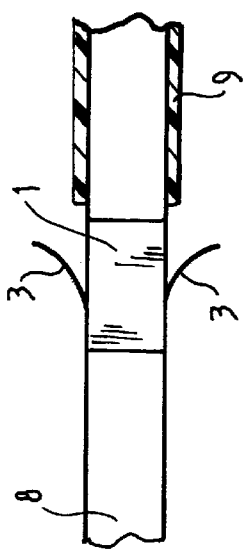
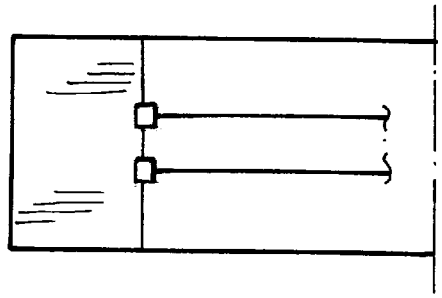
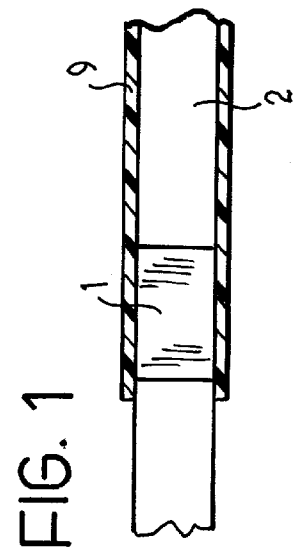

ELEMENT FOR ANCHORING AN IMPLANT DEVICE IN PLACE

FIELD OF THE INVENTION

The present invention concerns elements for anchoring implant devices in place.

The invention has been developed with particular attention to its possible application to the anchorage in place of implant devices such as electrodes for endocardial stimulation or drug delivery devices. The invention can nevertheless be used for the anchorage in place of a wide range of implant devices: some possible examples include vascular grafts, stents for angioplasty, various kinds of prosthetic cardiac valves, etc.

BACKGROUND OF THE INVENTION

Various arrangements have been proposed and utilised in order to anchor implant devices firmly in place, from suturing (consider, for example, the attachment of prosthetic cardiac valves), to retention effected by the expansion of the device in situ (one typically thinks of stents for angioplasty), to the deployment of mechanical attachment elements.

All of these above-described arrangements have greater or lesser disadvantages.

Attachment by means of suturing nearly always requires accessibility to the implant site from the outside and it is therefore practical only during surgery. Anchorage by way of expansion in situ carries the risk of the subsequent collapse of the device and is therefore practical only where particular conditions exist for the geometric coupling between the device and the associated implant site. Even mechanical attachment such as that utilised, for example, for pacemaker electrodes, often requires direct access to the implant site from the outside. Where implantation is preceded, for example, by catheterisation, the risk exists that attachment may occur before the device has reached the desired implantation site, locking the device itself in an undesirable position, when it can often be dangerous, if not impossible, to remove or reposition it.

SUMMARY OF THE INVENTION

The object of the present invention is to provide a solution which overcomes in radical manner the disadvantages described above.

According to the present invention, this object is achieved by virtue of an attachment element for implant devices having the characteristics specified in the following claims.

This invention is element for anchoring an implant device in place, comprising shape memory material so that the element is capable of passing, on reaching a transition temperature, from a substantially retracted position with respect to the associated implant device to an expanded position in which the element itself is capable of anchoring the device to an implant site. Preferably, the shape memory material reaches the transition temperature on being heated to the transition temperature. The transition temperature corresponds substantially to the temperature of the human body.

In a preferred embodiment, the element further comprises associated containment means for preventing the element itself from passing from the substantially retracted position to the expanded position on exposure of the shape memory material to the temperature of the human body during the insertion of the device towards the implant site. The element may comprise associated thermal insulation means for insulating the shape memory material from the temperature of the human body during the insertion of the device towards the implant site.

The implant device may also have an associated introduction catheter. In another preferred embodiment, associated with the element is a sheath or covering over the catheter and movable between a containment position in which the sheath or covering itself engages the element and a retracted position in which the sheath or covering disengages the element, thereby releasing it. Part of the sheath or covering capable of engaging the element preferably comprises thermal insulation material. The element may also carry an associated temperature control means. The temperature control means may be an electric resistor. The temperature control means also may extend at least partly into the element or may be generally outside the element.

Preferably, in the expanded position, the element has a general hook-like configuration and is more preferably in a general corkscrew or pig-tail-like conformation. Alternatively, the element may be in the form of a pair of corresponding anchorage elements which, in the extended position, extend from the associated implant device in a general arrow head-like configuration.

BRIEF DESCRIPTION OF THE DRAWINGS

The invention will now be described, purely by way of non-limiting example, with reference to the accompanying drawings, in which:

FIGS. 1 and 2 show schematically the application of an anchorage element according to the invention to a first implant device;

FIGS. 3 and 4 schematically illustrates the application of another anchorage element according to the invention to a different implant device; and FIG. 5 is a view on an enlarged scale of the part indicated by the arrow V in FIG. 4.

DETAILED DESCRIPTION OF THE PREFERRED EMBODIMENTS

In FIGS. 1 and 2, the reference numeral 1 illustrates schematically an implant device constituted, in the embodiment illustrated—which is by way of example and must not therefore be interpreted as limiting the scope of the invention—by an electrode intended to be implanted in the body of a patient. This may be, for example, a stimulation and/or detection electrode in a cardiac stimulation system (a pacemaker or defibrillator, for example). Alternatively, it could be a completely different type of implant device such as, for example, a drug dispenser or an element for attaching a vascular graft.

Specifically, the device 1 is intended to be put in place by catheterisation and, to this end, it is mounted (according to well-known criteria) on an introduction catheter 2 (of widely known type).

Thus, as can be seen more clearly in FIG. 2, the device 1 has at least one or, preferably, at least two associated attachment members 3, each constituted (completely as in the embodiment illustrated, or partly, for example, in the base only) by a kind of finger 3 capable of moving from a retracted or concealed position (illustrated in FIG. 1) in which, in practice, the elements 3 do not project beyond the contour of the device 1/catheter 2 assembly, to an expanded position (illustrated in FIG. 2) in which the fingers 3 project from the sides of the device 1. It is therefore clear that when the elements 3 are retracted, the device can be introduced into a patient's body, usually endovenously, and moved using the catheter until it reaches the implant site. The elements 3 can then be expanded in order to retain the device 1 at the implant site in a general arrangement which can be defined as an anchor, or even better, as an arrow head or fish hook.

FIGS. 3 to 5 illustrate another implant device, also indicated 1 (but nevertheless capable assuming the form of a different kind of implant device: in relation to this, reference should be made to the above description of the device illustrated in FIGS. 1 and 2) and located at the distal end of an associated catheter 2, this also being of known type.

In this case, the anchorage element, indicated 4, is constituted by a kind of spring which, starting from a folded or concealed position (illustrated in FIG. 3) in which the element 4 does not project beyond the profile of the distal end of the device 1/catheter 2 assembly, is capable of moving to an expanded position (illustrated in FIG. 4) in which the element 4 projects forward from the aforesaid distal end in a general arrangement which may be described as the end of a corkscrew or pig tail: it is therefore an arrangement adopted in many mechanical attachment devices of the type used, for example, in pacemaker electrodes.

Passing from the retracted or concealed position (FIGS. 1 and 3) to the expanded position (shown in FIGS. 2 and 4) is achieved according to the invention by virtue of a shape memory mechanism.

The physical mechanism known as a "shape memory" is widely known in the art and has been used for various purposes over a long time. In particular, numerous metal materials exist, for example, alloys based on the material known commercially as Nitinol (constituted essentially by nickel and titanium) that are capable of employing this mechanism: in practice, a body made from a shape memory material initially has a certain geometry or shape; on reaching a predetermined transition temperature (which can be by way of heating or possibly cooling), the material "remembers" that it can assume a different shape, and the body changes its geometry. In the specific embodiment illustrated by way of example, the elements 3 and 4 are formed such that they initially present the retracted shape (FIGS. 1 and 3) as long as they are kept below a predetermined temperature level at which they are able (by the effect of the shape memory mechanism upon reaching the aforesaid transition temperature) to move into the expanded configuration (FIGS. 2 and 4).

This result may be achieved in various ways.

For example, as illustrated schematically in FIG. 5, a heating device such as, for example, an electric resistor 6 may be provided inside the element 4. This resistor may be supplied by associated service wires 7 which pass along the catheter 2 to connect with the heating element in the element 4 by means of associated connectors 8. Once the locating operation has been completed, that is, after the device 1 has been taken to the desired position with the anchorage element 4 in the retracted position, the element 4 itself is heated to take it to the transition temperature and thus to pass to the expanded position so as to anchor the device 1 firmly to the implant site, for example, by "screwing" it to the surrounding tissues. This latter is effected by acting on the catheter 2 to cause an axial rotation of the device 1.

The catheter 2 may then be removed (according to known criteria) by disengaging it from the device 1 which remains in place, held by the element 4.

Due to this movement, the connectors 8 disengage from the heating element 6, disconnecting it from the associated service wires 7.

Naturally, this is one of many possible solutions. In particular, in some applications, the catheter may remain permanently implanted, for example, to enable electrostimulation and/or the delivery of drugs.

As has already been said, the shape memory mechanism may be primed, at least in theory, by cooling the elements 3 or 4. It follows that the heating resistor can be substituted by a cooling element such as, for example, an element having a Peltier effect, capable of cooling the element 3 or 4 in question until it reaches the temperature at which the element itself passes into the expanded position.

For other reasons, it is not strictly necessary that the temperature control element (whether a heating element such as the resistor 6, or a cooling element) also extends into the element 4. In order to achieve the necessary temperature control (heating or cooling), it is also possible to operate using an element associated with the distal end of the catheter 2 and capable of transferring the heat generated thereby to the element 4.

The desired expansion of the element 3 or 4 following the temperature control thereof can also be achieved without recourse to a positive action induced from the outside.

For example, the desired heating effect and expansion of the element 3, 4 can be achieved simply by exposing the element 3, 4 to the heat of the human body: in this case, it is of course important to ensure that the transition temperature at which the aforesaid shape memory mechanism operates coincides with the typical temperature of the human body (approximately 36–37° C.).

It is worth noting that when the thermal action of the human body is used in order to achieve the heating affect and the expansion of the element 3, 4, direct action must be taken in order to avoid the elements 3 or 4 expanding before the device 1 has reached the implant site.

One solution for avoiding this disadvantage is, for example, that of providing a mechanism which is intended to hold the elements 3, 4 in the retracted position until they reach the implant site where they are subsequently disengaged.

For example, FIGS. 1 and 2 show schematically an arrangement in which the aforesaid containment means for elements 3 are simply a kind of tubular sheath or covering 9 fitted over the catheter 2 with the ability to slide longitudinally between an initial position for the insertion and positioning of the device 1 (which position is represented in FIG. 1), in which the distal end of the covering 9 surrounds the device 1, withstanding and thus preventing the expansion of the elements 3, and a final position (shown in FIG. 2) in which, by sliding back along the body of the catheter 2 with a movement which can be controlled from the outside by the person operating the catheter, the covering 9 disengages the device 1, enabling the elements 3 to expand.

In addition or as an alternative, at least in part, to a mechanical containment action such as that described above, the covering 9 may be such as to have a heat insulating effect on the elements 3 (for example, due to the thermal insulation quality of the material forming at least the part intended to engage the elements 3) which is only seen when the covering 9 is withdrawn.

These are, of course, just some of the possible arrangements that can be adopted in order to achieve the desired result.

It can also be hypothesised, at least for devices 1 not intended for deep implantation in the human body (although the method is applicable, at least in theory, to all implant devices), to effect the insertion and positioning of the device 1 at the implant site by maintaining the patient in a state of hypothermia limited at least to path along which the device 1 is introduced. The normal thermal regime is then allowed to re-establish once the device 1 has reached the implant site, with the consequent expansion of the anchorage element 3, 4 due to the thermal action of the human body.

Naturally, the principle of the invention remaining the same, the details of manufacture and the embodiments may be widely varied with respect to those described and illustrated without by this departing from the ambit of the present invention. In particular, the anchorage element or elements 3, 4 may be configured so as to act, in addition to the anchoring affect, for example, as an electrode (for example for stimulation and/or sensing), or as a conduit for the delivery of drugs.

What is claimed is:

1. A system for anchoring an implant device at an implantation site within a human body comprising:

an implant device which maintains a substantially consistent shape during implantation in a human body;

an attachment element comprising shape memory material, the attachment element capable of passing, on reaching a transition temperature, from a substantially retracted position with respect to the implant device to an expanded position in which the attachment element is capable of anchoring the implant device at the implantation site; and a temperature controller positioned within the implant device, the temperature controller being thermally connected to the attachment element.

2. A system according to claim 1 wherein the temperature control means comprises an electric resistor.

3. A system according to claim 1 wherein the temperature control means extends at least partly into the element.

4. A system according to claim 2, wherein the electric resistor extends at least partly into the element.

5. A system according to claim 1, wherein the temperature control means is located substantially outside the element.

6. A system according to claim 2, wherein the temperature control means is located substantially outside the element.

7. A system according to claim 1, wherein the implant device comprises an electrode.

8. A system according to claim 1 wherein the implant device comprises a catheter.

9. A system according to claim 1 wherein the implant device comprises drug delivery means.

10. A system according to claim 1 wherein the temperature controller comprises a heating element.

11. A system according to claim 1 wherein the temperature controller comprises a cooling element.

12. A system according to claim 10 wherein the heating element comprises a resistor.

* * * * *